United States Patent [19]

Su et al.

[11] 4,191,832

[45] Mar. 4, 1980

[54] SEPARATION OF SYN AND ANTI OXIMES OF 1-SULFONYL-2-AMINOBENZIMIDAZOLES

[75] Inventors: Kenneth S. Su, Indianapolis; Robert J. Templeton; James H. Wikel, both of Greenwood, all of Ind.

[73] Assignee: Eli Lilly and Company, Indianapolis, Ind.

[21] Appl. No.: 19,526

[22] Filed: Mar. 12, 1979

[51] Int. Cl.$^2$ .......................................... C07D 235/30
[52] U.S. Cl. .................................................... 548/306
[58] Field of Search ........................................ 548/306

[56] References Cited

U.S. PATENT DOCUMENTS

| 4,008,243 | 2/1977 | Wikel et al. | 424/273 B |
| 4,118,573 | 10/1978 | Paget et al. | 548/306 |
| 4,118,742 | 10/1978 | Paget et al. | 548/306 |

*Primary Examiner*—Natalie Trousof
*Attorney, Agent, or Firm*—Charles W. Ashbrook; Arthur R. Whale

[57] ABSTRACT

Syn and anti oximes of 1-sulfonyl-2-aminobenzimidazoles are separated by selective crystallization.

6 Claims, No Drawings

SEPARATION OF SYN AND ANTI OXIMES OF 1-SULFONYL-2-AMINOBENZIMIDAZOLES

BACKGROUND OF THE INVENTION

A number of substituted benzimidazoles recently have been discovered which display unusually good antiviral activity; see for example U.S. Pat. Nos. 4,008,243, 4,118,573 and 4,018,790. Among the most active of such benzimidazole antiviral agents are a group of oximes which are 1-sulfonyl-2-amino (or acylamino)-5(6)-hydroximinomethylbenzimidazole derivatives. These compounds are disclosed by Paget et al. in U.S. Pat. No. 4,118,742. As pointed out in the reference, the oximes are prepared by first reacting the corresponding 1-sulfonyl-2-amino (or acylamino)-5(6)-acylbenzimidazoles with hydroxylamine. As might be expected, such procedure affords a mixture, generally a 50:50 mixture, of the syn oxime and the anti oxime. While both the syn and anti isomers display useful antiviral activity, the anti has been determined to be about eight times more potent than the corresponding syn isomer. It therefore would be desirable to have an efficient process for separating such syn and anti isomers. Paget et al. teaches that the syn and anti isomers of a 6-($\alpha$-acetoxyiminobenzyl)benzimidazole can be separated by selective crystallization from ethanol and chloroform. Paget et al. additionally teaches that 1.0 g. of 1-isopropylsulfonyl-2-amino-6-($\alpha$-hydroxyiminobenzyl)-benzimidazole can be chromatographed over a high pressure chromatography column using a 50:50 methanol-water eluant to provide 70 mg of 1-isopropylsulfonyl-2-amino-6-(anti-$\alpha$-hydroxyiminobenzyl)benzimidazole and 30 mg. of the corresponding syn isomer. These processes suffer in several respects. First, substantial product loss is encountered. Secondly, neither process affords an isomer in greater than about eighty percent purity. Moreover, chromatographic separation is time consuming and does not lend itself to large scale production.

An object of this invention is to provide a process for separating syn and anti oximes so that the respective isomers can be obtained in greater than about ninety-five percent purity. Another object is to provide a process whereby commercial quantities of anti oximes can be separated from the corresponding syn oximes.

SUMMARY OF THE INVENTION

In accordance with the present invention, there is provided a process for separating the syn and anti isomers of compounds having the formula

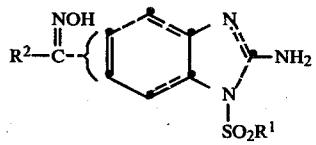

wherein:
$R^1$ is $C_1-C_5$ alkyl;
$R^2$ is phenyl, or phenyl substituted by $C_1-C_4$ alkyl, $C_1-C_4$ alkoxy, chloro, bromo, iodo, nitro or trifluoromethyl, comprising dissolving a mixture of syn and anti oximes in a water miscible organic solvent selected from acetone, methyl ethyl ketone, methanol, ethanol, isopropanol, acetonitrile, dimethylacetamide and dimethyl sulfoxide, adding a sufficient quantity of water to initate crystallization, and separating the precipitated anti oxime isomer.

A preferred organic solvent for use in the process is acetone. A particularly preferred aspect of the invention is the separation of syn and anti oximes of the above formula wherein $R^1$ is $C_1-C_3$ alkyl, and $R^2$ is phenyl.

The most preferred aspect of the invention is the separation of syn and anti isomers of 1-isopropylsulfonyl-2-amino-6-($\alpha$-hydroxyiminobenzyl)benzimidazole by dissolving the mixture in acetone and adding water to effect crystallization of the anti isomer. According to such method, 1-isopropylsulfonyl-2-amino-6-(anti-$\alpha$-hydroxyiminobenzyl)benzimidazole is recovered in greater than about ninety-six percent purity.

DETAILED DESCRIPTION OF THE INVENTION

All of the compounds which are purified according to the method of this invention are prepared according to the procedures set forth in U.S. Pat. No. 4,118,742. The syn and anti oximes which are prepared by the method of this invention have the formulas

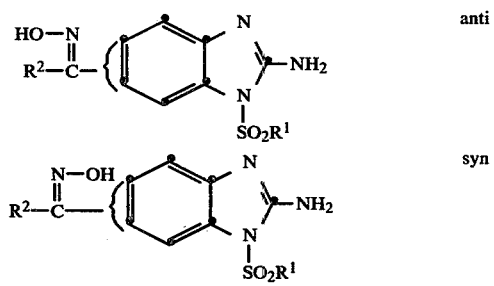

The method of this invention is carried out by dissolving a mixture of syn and anti oximes, which compounds are defined by the above formulas, in a water miscible organic solvent. Suitable solvents include ketones such as acetone and methyl ethyl ketone; alcohols such as methanol, ethanol and isopropanol; nitriles such as acetonitrile; amides such as acetamide; and sulfoxides such as dimethyl sulfoxide. The amount of organic solvent is not a critical factor. However, sufficient organic solvent should be utilized to completely dissolve the oxime. If desired, the organic solvent can be heated to a temperature of about 30 to about 100° C. in order to facilitate dissolution. Once the oxime has dissolved in the organic solution, it may be desirable to filter the solution in an effort to remove any foreign material or any undissolved oxime. Decolorizing agents and filter aids can be utilized if desired. The organic solution of oxime is next stirred at a temperature of about 5° to about 50° C., preferably at about 20° to 30° C., and sufficient water is added to initiate precipitation. Typically the volume of water utilized is about equal to the volume of organic solvent utilized. Once the water is added to the solution, stirring is generally continued for about 10 to about 90 minutes, or longer if desired, so as to permit substantially all of the anti oxime isomer to crystallize. Such anti isomer is then recovered by simply filtering the reaction mixture, for instance by gravity or with the assistance of reduced pressure. The anti oxime thus recovered generally is greater than about ninety-five percent pure (i.e. no more than about five percent of the syn isomer is admixed with the anti). The anti oxime can of course be further purified by normal crystallization from common solvents such as acetonitrile and the like.

According to the method of this invention, the syn oxime isomer surprisingly remains substantially dissolved in the organic solvent and water mixture, thereby permitting the isolation of the corresponding anti oxime isomer in nearly quantitative yield and in substantially pure form. The syn isomer remains in the filtrate and can be isolated if desired by simply removing the solvent from the filtrate, for example by evaporation under reduced pressure and/or lyophilization. The syn oxime can be further purified if needed by recrystallization from common solvents such as methanol and the like. As pointed out in U.S. Pat. 4,118,742, the oximes of the above formula are useful as antiviral agents. The anti oximes are of particular importance due to their potency against viruses such as Coxsackie, echovirus, Mengo, rhinovirus and Polio virus. The compounds may thus be useful in the treatment of common colds and related disorders.

The following detailed examples are illustrative of the invention and are not intended to limit the scope thereof.

EXAMPLE 1

1-Isopropylsulfonyl-2-amino-6-(anti-α-hydroxyiminobenzyl)benzimidazole

A slurry of 5.0 g. of a mixture consisting of about sixty percent of 1-isopropylsulfonyl-2-amino-6-(anti-α-hydroxyiminobenzyl)benzimidazole and about forty percent of the corresponding syn isomer in 100 ml. of acetone was stirred and heated to about 80° C. in order to obtain a clear solution. The solution thus obtained was cooled to room temperature and gravity filtered. The filter was washed with 10 ml. of fresh acetone, which was added directly to the filtrate. The filtrate was stirred and 120 ml. of water was added to it portionwise over ten minutes. Following complete addition of the water, the mixture was stirred for an additional twenty minutes at room temperature. The precipitated solid which had formed was collected by filtration and air dried to give 2.4 g. of 1-isopropylsulfonyl-2-amino-6-(anti-α-hydroxyiminobenzyl)benzimidazole. The product was shown by high pressure liquid chromatography to consist of 95 percent of the anti isomer and 5 percent of the corresponding syn isomer.

The anti oxime thus obtained was recrystallized from 150 ml. of acetonitrile to afford 1.6 g. of 1-isopropylsulfonyl-2-amino-6-(anti-α-hydroxyiminobenzyl)benzimidazole, which was shown to contain no more than about 2.8 percent of the corresponding syn isomer.

EXAMPLE 2

1-Isopropylsulfonyl-2-amino-6-(anti-α-hydroxyiminobenzyl)benzimidazole

A solution of 100.0 of a 60:40 anti-syn mixture of 1-isopropylsulfonyl-2-amino-6-(α-hydroxyiminobenzyl)benzimidazole in 2000 ml. of acetone was heated to 90° C. and stirred while 10.0 g. of Norite decolorizing carbon was added portionwise. The mixture was stirred for an additional five minutes and then gravity filtered. The filtrate was cooled to room temperature and stirred while 2800 ml. of water was added portionwise over twenty minutes. The aqueous mixture was next stirred for one hour, and then was filtered. The precipitate thus collected was air dried and identified by high pressure liquid chromatography to consist of greater than 95 percent 1-isopropylsulfonyl-2-amino-6-(anti-α-hydroxyiminobenzyl)benzimidazole.

The anti isomer thus formed was recrystallized from 1600 ml. of acetonitrile to give 98 percent pure 1-isopropylsulfonyl-2-amino-6-(anti-α-hydroxyiminobenzyl)benzimidazole.

EXAMPLE 3

The acetone-water filtrate from Example 2 was concentrated to give a solid which, after crystallization from acetonitrile, was shown to be greater than 95 percent pure 1-isopropylsulfonyl-2-amino-6-(syn-α-hydroxyiminobenzyl)benzimidazole.

We claim:

1. A process for separating syn and anti oximes of the formula

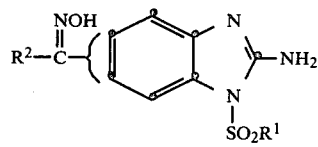

wherein:

$R^1$ is $C_1$–$C_5$ alkyl; and $R^2$ is phenyl, or phenyl substituted by $C_1$–$C_4$ alkyl, $C_1$–$C_4$ alkyl, $C_1$–$C_4$ alkoxy, chloro, bromo, iodo, nitro or trifluoromethyl, comprising dissolving a mixture of syn and anti oximes in a water mixcible organic solvent selected from acetone, methyl ethyl ketone, methanol, ethanol, isopropanol, acetonitrile, dimethylacetamide and dimethyl sulfoxide, adding a sufficient quantity of water to initate crystallization, and separating the precipitated anti oxime isomer.

2. The process of claim 1 wherein the organic solvent is acetone.

3. The process of claim 1 wherein the organic solvent is methanol.

4. The process of claim 1 wherein the organic solvent is acetonitrile.

5. The process of claim 2 wherein $R^1$ is $C_1$–$C_3$ alkyl, and $R^2$ is phenyl.

6. The process of claim 5, said process comprising dissolving a syn-anti mixture of 1-isopropylsulfonyl-2-amino-6-(α-hydroxyiminobenzyl)benzimidazole in acetone and adding sufficient water to initiate precipitation, and separating the solid 1-isopropylsulfonyl-2-amino-6-(anti-α-hydroxyiminobenzyl)benzimidazole.

* * * * *